(12) United States Patent
Gérard et al.

(10) Patent No.: US 10,968,228 B2
(45) Date of Patent: Apr. 6, 2021

(54) METHODS OF PREPARING SUBSTITUTED 12A,13-DIHYDRO-6H-BENZO[5,6][1,4] DIAZEPINO[1,2-A]INDOLES

(71) Applicant: IMMUNOGEN, INC., Waltham, MA (US)

(72) Inventors: Baudouin Gérard, Belmont, MA (US); Richard A. Silva, Needham, MA (US); Michael Louis Miller, Framingham, MA (US); Manami Shizuka, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 16/560,379

(22) Filed: Sep. 4, 2019

(65) Prior Publication Data

US 2020/0109145 A1    Apr. 9, 2020

Related U.S. Application Data

(62) Division of application No. 15/956,835, filed on Apr. 19, 2018, now Pat. No. 10,442,809.

(60) Provisional application No. 62/487,695, filed on Apr. 20, 2017.

(51) Int. Cl.
*C07D 487/22* (2006.01)
*C07D 487/04* (2006.01)
*C07D 209/12* (2006.01)

(52) U.S. Cl.
CPC ......... *C07D 487/04* (2013.01); *C07D 209/12* (2013.01)

(58) Field of Classification Search
CPC .................................................. C07D 487/22

USPC ......................................................... 540/579
See application file for complete search history.

(56) References Cited

U.S. PATENT DOCUMENTS 10,442,809 B2    10/2019    Gerard et al.

FOREIGN PATENT DOCUMENTS

WO    2010/091150 A1    8/2010
WO    2012/128868 A1    9/2012

OTHER PUBLICATIONS

Ramadas et al., Iron-Ammonium Chloride—A Convenient and Inexpensive Reductant. Synthetic Communications. Dec. 1992;22(22):3189-3195.

*Primary Examiner* — Douglas M Willis
(74) *Attorney, Agent, or Firm* — McCarter & English, LLP; Steven G. Davis; Xin Zhang

(57) ABSTRACT

The invention provides novel methods for preparing indolinobenzodiazepine monomer compounds of formula (I) below and their synthetic precursors:

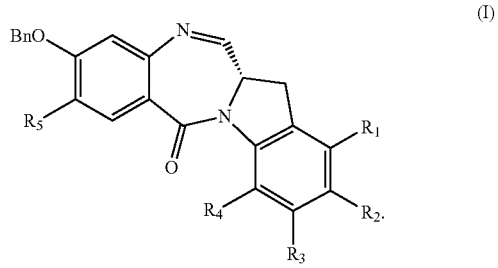

(I)

20 Claims, No Drawings

METHODS OF PREPARING SUBSTITUTED 12A,13-DIHYDRO-6H-BENZO[5,6][1,4] DIAZEPINO[1,2-A]INDOLES

RELATED APPLICATION

This application is a divisional of U.S. patent application Ser. No. 15/956,835, filed Apr. 19, 2018, which claims the benefit of the filing date, under 35 U.S.C. § 119(e), of U.S. Provisional Application No. 62/487,695, filed on Apr. 20, 2017, the entire contents of which are incorporated herein by reference.

FIELD OF THE INVENTION

The present invention relates to novel methods for preparing indolinobenzodiazepine derivatives.

BACKGROUND OF THE INVENTION

Benzodiazepine derivatives are useful compounds for treating various disorders, and include medicaments such as, antiepileptics (imidazo [2,1-b][1,3,5] benzothiadiazepines, U.S. Pat. Nos. 4,444,688; 4,062,852), antibacterials (pyrimido[1,2-c][1,3,5]benzothiadiazepines, GB 1476684), diuretics and hypotensives (pyrrolo(1,2-b)[1,2,5]benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

Recently, it has been shown that cell-binding agent conjugates of indolinobenzodiazepine dimers can inhibit tumor growth both in vitro and in vivo in animal models. See, example, WO 2010/091150, WO 2016/036801, WO 2016/036804. Further, cell-binding agent conjugates of indolinobenzodiazepine dimers that have one imine functionality and one amine functionality have been to shown to display a much higher therapeutic index (ratio of maximum tolerated dose to minimum effective dose) in vivo compared to previously disclosed benzodiazepine derivatives having two imine functionalities. See, for example, WO 2012/128868.

Thus, there exists a need for improved methods for preparing the indolinobenzodiazepine monomer precursors that are more efficient and suitable for large scale manufacturing process for making the cytotoxic indolinobenzodiazepine dimer compounds.

SUMMARY OF THE INVENTION

The present invention provides improved synthetic methods for preparing indolinobenzodiazepine monomer compounds and their synthetic precursors. Compared to the previously disclosed methods, the methods of the present invention are more suitable for large scale manufacturing process.

In one embodiment, the present invention provides a method of preparing a compound of formula (I):

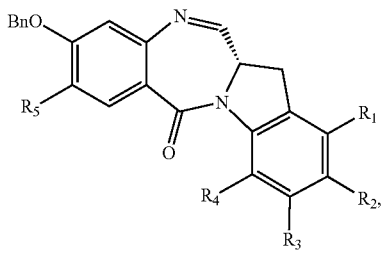

(I)

or a salt thereof, comprising reacting the compound of formula (II):

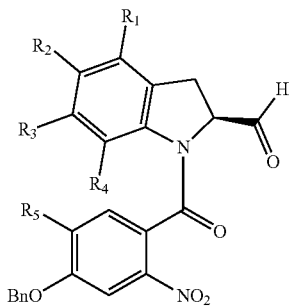

(II)

or a salt thereof, with Fe in the presence of $NH_4Cl$, wherein:

$R_1$, $R_2$, $R_3$, and $R_4$ are each independently selected from —H, an optionally substituted linear, branched or cyclic alkyl, alkenyl or alkynyl having from 1 to 10 carbon atoms, —$(CH_2CH_2X)_n$—$R^c$, halogen, —NH(C=NH)$NH_2$, —OR, —NR'R", —NCO, —NR'COR", —SR, —SOR', —$SO_2$R', —$SO_3$H, —$OSO_3$H, —$SO_2$NR'R", cyano, azido, —COR', —OCOR', and —OCONR'R";

X is O, NH or S;

$R_5$ is —H, —R, —OR, —SR, —NR'R", or halogen;

R, for each occurrence, is independently selected from —H, an optionally substituted linear, branched or cyclic alkyl, alkenyl or alkynyl having from 1 to 10 carbon atoms, a polyethylene glycol unit —$(CH_2CH_2X)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —$NR_2$, —COR, an optionally substituted linear, branched or cyclic alkyl, alkenyl or alkynyl having from 1 to 10 carbon atoms, a polyethylene glycol unit —$(CH_2CH_2X)_n$—$R^c$, and an optionally substituted 3- to 18-membered heterocyclic ring having 1 to 6 heteroatoms independently selected from O, S, N and P;

$R^c$ is —H or a substituted or unsubstituted linear or branched alkyl having 1 to 4 carbon atoms; and n is an integer from 1 to 24.

In another embodiment, the present invention provides a method of preparing a compound of formula (III):

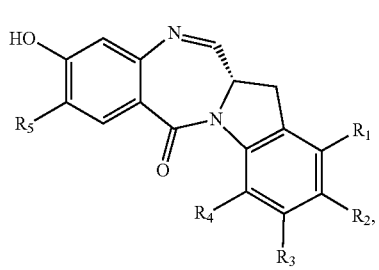

(III)

or a salt thereof, comprising reacting the compound of formula (I):

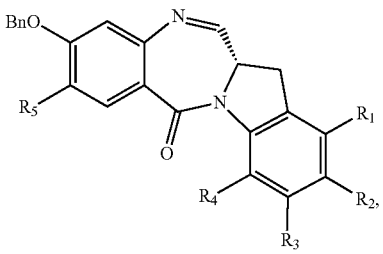

(I)

or a salt thereof, with a hydrogenation reagent in the presence of a palladium catalyst, wherein the variables are defined above.

In yet another embodiment, the present invention provides a method of preparing a compound of formula (III):

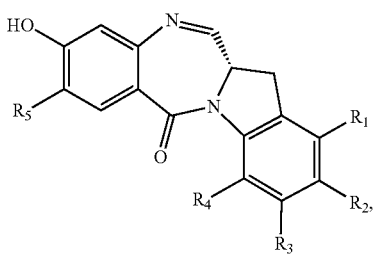

(III)

or a salt thereof, comprising the steps of:

a) reacting the compound of formula (II):

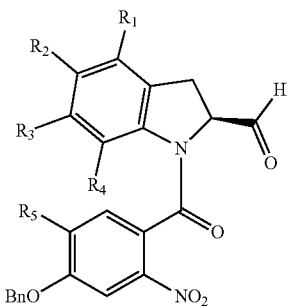

(II)

with Fe in the presence of $NH_4Cl$ to form a compound of formula (I):

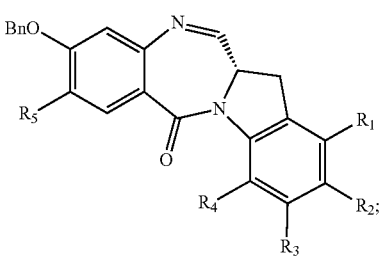

(I)

and b) reacting the compound of formula (I) with a hydrogenation reagent in the presence of a palladium catalyst to form the compound of formula (III), wherein the variables are as defined above.

The present invention also provide compounds described herein, such as compounds of formula (IV), (V), (IVA), (VA) or a salt thereof.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

It should be understood that any of the embodiments described herein can be combined with one or more other embodiments of the invention, unless explicitly disclaimed or improper. Combination of embodiments are not limited to those specific combinations claimed via the multiple dependent claims.

1. Definitions

"Alkyl' as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms. Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alky group or $C_3$-$C_6$ for branched chain alkyl). Examples of alkyl include, but are not limited to, methyl, ethyl, 1-propyl, 2-propyl, 1-butyl, 2-methyl-1-propyl, —$CH_2CH(CH_3)_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, ($C_x$-$C_{xx}$)alkyl or $C_x$alky means a linear or branched alkyl having x-xx carbon atoms.

"Alkenyl" as used herein refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like. Preferably, the alkenyl has two to ten carbon atoms. More preferably, the alkyl has two to four carbon atoms.

"Alkynyl" as used herein refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. As used herein, the term refers to the radical of a saturated ring. In preferred embodiments, cycloalkyls have from 3-10 carbon atoms in their ring structure, and more preferably from 5-7 carbon atoms in the ring structure. In some embodiments, the two cyclic rings can have two or more atoms in common, e.g., the rings are "fused rings." Suitable cycloalkyls include cycloheptyl, cyclohexyl, cyclopentyl, cyclobutyl and cyclopropyl. In some embodiments, the cycloalkyl is a mono-cyclic group. In some embodiments, the cycloalkyl is a bi-cyclic, group. In some embodiments, the cycloalkyl is a tri-cyclic group.

The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 atoms in the ring, preferably from 5 to 7. For example, aryl groups include, but are not limited to, phenyl (benzene), tolyl, anthracenyl, fluorenyl, indenyl, azulenyl, and naphthyl, as well as benzo-fused carbocyclic moieties such as 5,6,7,8-tetrahydronaphthyl, and the like In some embodiments, the aryl is a single-ring aromatic group. In some embodiments, the aryl is a two-ring aromatic group. In some embodiments, the aryl is a three-ring aromatic group.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofurane, tetrahydrothiene, tetrahydropyrane, dihydropyrane, tetrahydrothiopyranyl, thiomorpholine, thioxane, homopiperazine, azetidine, oxetane, thietane, homopiperidine, oxepane, thiepane, oxazepine, diazepine, thiazepine, 2-pyrroline, 3-pyrroline, indoline, 2H-pyrane, 4H-pyrane, dioxanyl, 1,3-dioxolane, pyrazoline, dithiane, dithiolane, dihydropyrane, dihydrothiene, dihydrofurane, pyrazolidinylimidazoline, imidazolidine, 3-azabicyco[3.1.0]hexanyl, 3-azabicyclo[4.1.0]heptane, and azabicyclo[2.2.2]hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heteroaryl" as used herein, refers to substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more carbons are common to two adjoining rings, e.g., the rings are "fused rings," wherein at least one of the rings is heteroaromatic, e.g., the other cyclic rings can be cycloalkyls, cycloalkenyls, cycloalkynyls, aryls, and/or heterocyclyls. In some preferred embodiments, preferred polycycles have 2-3 rings. In certain embodiments, preferred polycyclic ring systems have two cyclic rings in which both of the rings are aromatic. In certain embodiments, each ring of the polycycle contains from 3 to 10 atoms in the ring, preferably from 5 to 7. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like.

In some embodiments, the heteroaryl is a single-ring aromatic group. In some embodiments, the heteroaryl is a two-ring aromatic group. In some embodiments, the heteroaryl is a three-ring aromatic group.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2 pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

The term "halide" or "halogen" refers to F, Cl, Br or I. In one embodiment, the halide is Cl.

The term "compound" is intended to include compounds for which a structure or formula or any derivative thereof has been disclosed in the present invention or a structure or formula or any derivative thereof that has been incorporated by reference. The term also includes, stereoisomers, geometric isomers, or tautomers. The specific recitation of "stereoisomers," "geometric isomers," "tautomers," "salt" in certain aspects of the invention described in this application shall not be interpreted as an intended omission of these forms in other aspects of the invention where the term "compound" is used without recitation of these other forms.

The term "precursor" of a given group refers to any group which may lead to that group by any deprotection, a chemical modification, or a coupling reaction.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "salt" as used herein, refers to an organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A salt may involve the inclusion of another molecule such as an acetate ion, a succinate ion or other counter ion. The counter ion may be any organic or inorganic moiety that stabilizes the charge on the parent compound. Furthermore, a salt may have more than one charged atom in its structure. Instances where multiple charged atoms are part of the salt can have multiple counter ions. Hence, a salt can have one or more charged atoms and/or one or more counter ion.

If the compound of the invention is a base, the desired salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

2. Methods of the Present Invention

In a first embodiment, the present invention provides a method of preparing a compound of formula (I):

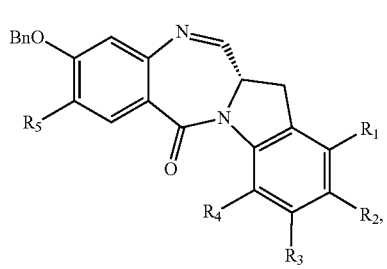

(I)

or a salt thereof, comprising reacting the compound of formula (II):

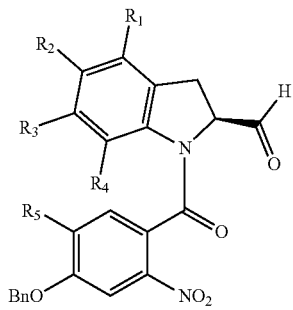

(II)

or a salt thereof, with Fe in the presence of NH₄Cl, wherein:

R₁, R₂, R₃, and R₄ are each independently selected from —H, an optionally substituted linear, branched or cyclic alkyl, alkenyl or alkynyl having from 1 to 10 carbon atoms, —(CH₂CH₂X)$_n$—R$^c$, halogen, —NH(C=NH)NH₂, —OR, —NR'R", —NCO, —NR'COR", —SR, —SOR', —SO₂R', —SO₃H, —OSO₃H, —SO₂NR'R", cyano, azido, —COR', —OCOR', and —OCONR'R";

X is O, NH or S;

R₅ is —H, —R, —OR, —SR, —NR'R", or halogen;

R, for each occurrence, is independently selected from —H, an optionally substituted linear, branched or cyclic alkyl, alkenyl or alkynyl having from 1 to 10 carbon atoms, a polyethylene glycol unit —(CH₂CH₂X)$_n$—R$^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;

R' and R" are each independently selected from —H, —OH, —OR, —NHR, —NR₂, —COR, an optionally substituted linear, branched or cyclic alkyl, alkenyl or alkynyl having from 1 to 10 carbon atoms, a polyethylene glycol unit —(CH₂CH₂X)$_n$—R$^c$, and an optionally substituted 3- to 18-membered heterocyclic ring having 1 to 6 heteroatoms independently selected from O, S, N and P;

R$^c$ is —H or a substituted or unsubstituted linear or branched alkyl having 1 to 4 carbon atoms; and n is an integer from 1 to 24.

In a second embodiment, the present invention provide a method of preparing a compound of formula (IA):

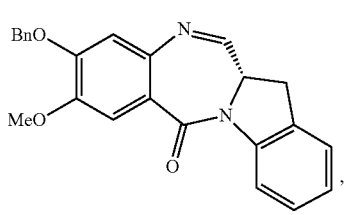

(IA)

or a salt thereof, comprising reacting the compound of formula (IIA):

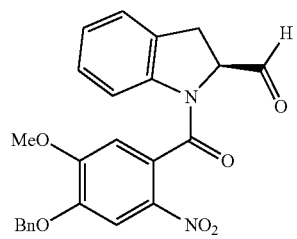

(IIA)

or a salt thereof, with Fe in the presence of NH₄Cl.

In a third embodiment, the present invention provides a method of preparing a compound of formula (III):

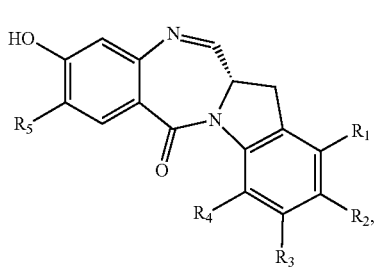

(III)

or a salt thereof, comprising reacting the compound of formula (I):

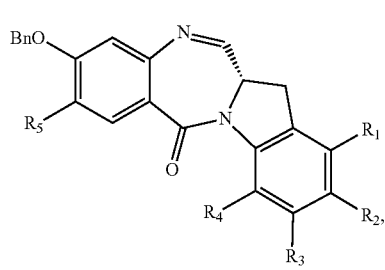

(I)

or a salt thereof, with a hydrogenation reagent in the presence of a palladium catalyst, wherein the variables are defined above in the first embodiment. The reaction of the compound of formula (I) with the hydrogenation reagent and the palladium catalyst de-benzylates the benzyl group to yield the compound of formula (III).

In a fourth embodiment, the present invention provides a method of preparing a compound of formula (IIIA):

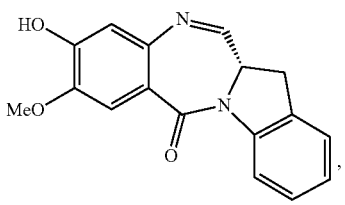
(IIIA)

or a salt thereof, comprising reacting the compound of formula (IA):

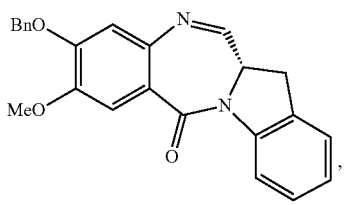
(IA)

or a salt thereof, with a hydrogenation reagent in the presence of a palladium catalyst.

In a fifth embodiment, the present invention provides a method of preparing a compound of formula (III):

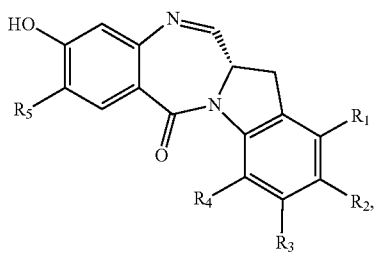
(III)

or a salt thereof, comprising the steps of:
a) reacting the compound of formula (II):

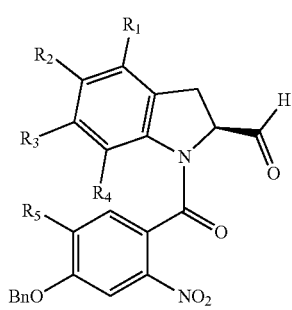
(II)

with Fe in the presence of NH$_4$Cl to form a compound of formula (I):

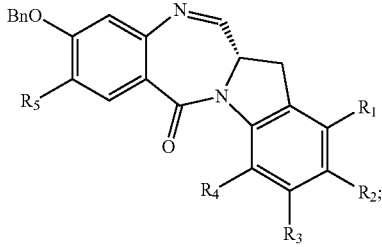
(I)

and
b) reacting the compound of formula (I) with a hydrogenation reagent in the presence of a palladium catalyst to form the compound of formula (III), wherein the variables are as defined above in the first embodiment.

In a sixth embodiment, the present invention provides a method of preparing a compound of formula (IIIA):

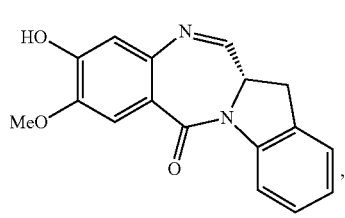
(IIIA)

or a salt thereof, comprising the steps of:
a) reacting the compound of formula (IIA):

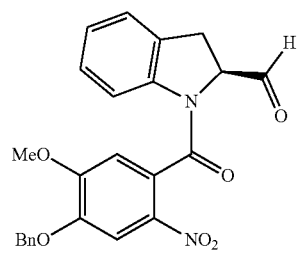
(IIA)

with Fe in the presence of NH$_4$Cl to form a compound of formula (IA):

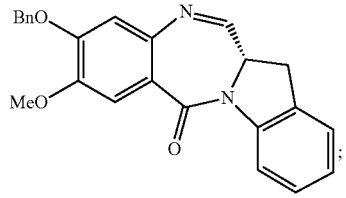
(IA)

and
b) reacting the compound of formula (IA) with a hydrogenation reagent in the presence of a palladium catalyst to form the compound of formula (IIIA).

In a 1$^{st}$ specific embodiment, for the method of the first, second, fifth or sixth embodiment, the reaction of the compound of formula (II) or (IIA) and Fe/NH$_4$Cl is carried out in a solvent or a solvent mixture. Any suitable solvent or solvent mixtures can be used. Exemplary solvents include, but are not limited to, tetrahydrofuran (THF), 2-methyltetrahydrofuran (MeTHF), N-methyl-2-pyrrolidone (NMP), methanol, ethanol, isopropanol, dichloromethane, dichloroethane, acetonitrile, dimethylformamide (DMF), dimethylacetamide, cyclopentyl methyl ether (CPME), ethyl acetate, water, and a combination thereof. In certain embodiment, the reaction is carried out in a mixture of water and one or more organic solvents. Any suitable organic solvents described above can be used. In a more specific embodiment, the reaction is carried out in a mixture of THF, methanol and water.

In a 2$^{nd}$ specific embodiment, for the method of the first, second, fifth or sixth embodiment or the 1$^{st}$ specific embodiment, the reaction between the compound of formula (II) or (IIA) and Fe/NH$_4$Cl is carried out at a temperature between 0° C. and 100° C., between 20° C. and 100° C., between 40° C. and 90° C., between 50° C. and 80° C., or between 60° C. and 70° C. In a more specific embodiment, the reaction is carried out at 65° C.

As used herein, the term "between number1 and number2" means a number that is greater or equal to number1 and less or equal to number2.

As used herein, the term "number1 to number2" means a number that is greater or equal to number1 and less or equal to number2.

In certain embodiments, for the method of the first, second, fifth or sixth embodiment or the 1$^{st}$ or 2$^{nd}$ specific embodiment, the reaction between the compound of formula (II) or (IIA) and Fe/NH$_4$Cl can be carried out for appropriate amount of time, such as 1 hour to 1 week, 4 hours to 72 hours, 10 hours to 72 hours, 24 hours to 72 hours, 4 hours to 10 hours, or 10 hours to 24 hours. In a specific embodiment, the reaction is carried out for 48 hours.

In certain embodiments, for the method of the first, second, fifth or sixth embodiment or the 1$^{st}$ or 2$^{nd}$ specific embodiment, the reaction between the compound of formula (II) or (IIA) and Fe/NH$_4$Cl is carried out under an inert atmosphere, such as under N$_2$, Ar etc. In a specific embodiment, the reaction is carried out under N$_2$ atmosphere. In certain embodiments, for the method of the first, second, fifth or sixth embodiment or the 1$^{st}$ or 2$^{nd}$ specific embodiment, the compound of formula (I) or (IA) obtained from the reaction between the compound of formula (II) or (IIA) and Fe/NH$_4$Cl is purified. Any suitable purification methods, such as precipitation, re-crystallization, column chromatography or a combination thereof, can be used. In certain embodiments, precipitation, re-crystallization, or a combination thereof can be used to purify the compound of formula (I) or (IA). Multiple (e.g., two, three, four, etc.) precipitations or re-crystallizations or a combination therefore can be used to purify the compound of formula (I) or (IA).

As used herein, "re-crystallization" refers to a process for purifying a solid material, wherein the atoms, molecules or ions of the purified solid material obtained are arranged in highly organized structure(s), known as crystalline form(s). Re-crystallization can be achieved by various methods, such as cooling, evaporation, addition of a second solvent (i.e., antisolvent), etc.

As used herein, "precipitation" refers to a purification process in which solid material forms from a solution having the solid material dissolved therein. Precipitation can often achieved by cooling down the temperature of the solution or adding a second solvent (i.e., antisolvent) that significantly reduce the solubility of the desired solid material in the solution. The solid material obtained from the precipitation process can be in one or more amorphous forms, one or more crystalline forms or a combination thereof.

In a 3$^{rd}$ specific embodiment, for the method of the first, second, fifth or sixth embodiment or the 1$^{st}$ or 2$^{nd}$ specific embodiment, the compound of formula (I) or (IA) obtained from the reaction between the compound of formula (II) or (IIA) and Fe/NH$_4$Cl is purified by re-crystallization or precipitation in a mixture of dichloromethane and ethanol. In a more specific embodiment, the volume ratio of dichloromethane and ethanol is between 5:1 and 1:2, between 4:1 and 1:1.5, between 3:1 and 1:1.5, or between 2:1 and 1:1.2. In a specific embodiment, the volume ratio of dichoromethane and ethanol is 1:1. In certain embodiments, the re-crystallization is carried out overnight.

Alternatively, the compound of formula (I) or (IA) is purified by re-crystallization or precipitation in a mixture of toluene and acetonitrile. In one embodiment, the compound of formula (I) or (IA) is dissolved in toluene at an elevated temperature, such as a temperature between 40° C. and 90° C., between 50° C. and 90° C., between 60° C. and 90° C., between 70° C. and 90° C., or between 75° C. and 85° C. In another even more specific embodiment, the compound of formula (I) or (IA) is dissolved in toluene at 80° C. followed by addition of acetonitrile, to re-crystalize or precipitate the compound of formula (I) or (IA). Optionally, the compound of formula (I) or (IA) is filtered after dissolution in toluene before the addition of acetonitrile. In one embodiment, the volume ratio of toluene and acetonitrile is between 1:10 and 2:1, between 1:5 and 1:1, between 1:3 and 1:1, or between 1:2 and 1:1. Ina specific embodiment, the volume ratio of toluene and acetonitrile is 1:1.5.

In a 4$^{th}$ specific embodiment, for the methods of the 3$^{rd}$ specific embodiment described above, the compound of formula (I) or (IA) is further purified by recrystallization or precipitation. In a more specific embodiment, the compound of formula (I) or (IA) is further purified by recrystallization or precipitation in a mixture of toluene and acetonitrile. In a even more specific embodiment, the compound of formula (I) or (IA) is dissolved in toluene at an elevated temperature, such as a temperature between 40° C. and 90° C., between 50° C. and 90° C., between 60° C. and 90° C., between 70° C. and 90° C., or between 75° C. and 85° C. In another even more specific embodiment, the compound of formula (I) or (IA) is dissolved in toluene at 80° C. followed by addition of acetonitrile, to re-crystalize or precipitate the compound of formula (I) or (IA). Optionally, the compound of formula (I) or (IA) is filtered after dissolution in toluene before the addition of acetonitrile. In one embodiment, the volume ratio of toluene and acetonitrile is between 1:10 and 2:1, between 1:5 and 1:1, between 1:3 and 1:1, or between 1:2 and 1:1. In a specific embodiment, the volume ratio of toluene and acetonitrile is 1:1.5.

In a 5$^{th}$ specific embodiment, for the method of the third, fourth, fifth or sixth embodiment or the 1$^{st}$, 2$^{nd}$, 3$^{rd}$ or 4$^{th}$ specific embodiment, the de-benzylation reaction of the compound of formula (I) or (IA) is carried out in the presence of a Pd/Alox (also known as palladium on alumina (i.e., aluminum oxide)) catalyst. Any suitable Pd/Alox catalysts can be used. Exemplary palladium/Alox catalysts include, but are not limited to, palladium on alumina 10% Pd basis (i.e., 10 w.t. % Pd/Alox), such as Sigma-Aldrich® #76000, palladium on alumina 5% Pd basis (i.e., 5 w.t. % Pd/Alox), such as Johnson Matthey 5R325 Powder, Johnson Matthey A302099-5, Noblyst® P1159, STREM 46-1960, 46-1951, palladium on alumina 0.5% Pd basis (i.e., 0.5 w.t.

% Pd/Alox), such as STREM 46-1920, Alfa Aesar #41383, #38786, #89114, #38289. In a more specific embodiment, the palladium catalyst is 5 w.t. % Pd/Alox (i.e., palladium on alumina 5% Pd basis).

In a 6$^{th}$ specific embodiment, for the method of the third, fourth, fifth or sixth embodiment or the 1$^{st}$, 2$^{nd}$, 3$^{rd}$ or 4$^{th}$ specific embodiment, the de-benzylation reaction of the compound of formula (I) or (IA) is carried out in the presence of Pd/C (also known as palladium on carbon). Any suitable Pd/C catalysts can be used. Exemplary Pd/C catalysts include, but are not limited to, palladium on activated carbon 20% Pd basis (i.e., 20 w.t. % Pd/C), such as STREM 46-1707, palladium on activated charcoal 10% Pd basis(i.e., 10 w.t. % Pd/C), such as Sigma-Aldrich® #75990, #75993, Johnson Matthey 10R39, 10R394, 10R487 Powder, 10R87L Powder, 10T755, Evonik Noblyst® P1070, STREM 46-1900, palladium on activated charcoal 5% Pd basis (i.e., 5 w.t. % Pd/C), such as Sigma-Aldrich® #75992, #75991, Johnson Matthey 5R338M, 5R369, 5R374, 5R39, 5R395, 5R424, 5R434, 5R437, 5R440, 5R452, 5R487, 5R487 Powder, 5R58, 5R87L, 5T761, A102023-5, A103023-5, A105023-5, A302002-5, A302023-10, A302023-5, A402028-10, A405028-5, A405032-5, A405129-5, A501023-10, A503002-5, A503023-5, A503032-5, A702023-10, STREM 46-1890, 46-1908, 46-1909, 46-1911, Eonik Noblyst® P1086, P1090, P1092, P1109, palladium on activated carbon 3% Pd basis (i.e., 3 w.t.% Pd/C), such as STREM 46-1907, palladium on activated carbon 0.5% Pd basis (i.e., 0.5 w.t.% Pd/Alox), such as Alfa Aesar #38289.

In a 7$^{th}$ specific embodiment, for the method of the 5$^{th}$ or 6$^{th}$ specific embodiment, the de-benzylation reaction of the compound of formula (I) or (IA) is carried out in the presence of 0.05 to 0.5 equivalent of Pd for every 1 equivalent of the compound of formula (I) or (IA). In one embodiment, between 0.05 and 0.4, between 0.05 and 0.35, between 0.05 and 0.3, between 0.05 and 0.25, between 0.05 and 0.2, between 0.05 and 0.15, between 0.075 and 0.15, between 0.075 and 0.1, or between 0.08 and 0.1 equivalent of Pd catalyst is used for every 1 equivalent of the compound of formula (I). In a more specific embodiment, 0.09 or 0.1 equivalent of the Pd catalyst is used for every 1 equivalent of the compound of formula (I). In another embodiment, the amount of the palladium catalyst used depends on the type and manufacturer of the palladium catalyst used and the suitable amount of the palladium catalyst can be determined experimentally.

In a 8$^{th}$ specific embodiment, for the method of the third, fourth, fifth or sixth embodiment or the 1$^{st}$, 2$^{nd}$, 3$^{rd}$, 4$^{th}$, 5$^{th}$, 6$^{th}$ or 7$^{th}$ specific embodiment, the de-benzylation reaction of the compound of formula (I) or (IA) is carried out in the presence of 1,4-cyclohexadiene and a palladium catalyst (e.g., those described in the 5$^{th}$ or 6$^{th}$ specific embodiment). In one embodiment, 1.0 to 5.0 equivalents of 1,4-cyclohexadiene is used for every 1 equivalent of the compound of formula (I) or (IA). In another embodiment, 1.0 to 4.5, 1.0 to 4.0, 1.0 to 3.5, 1.0 to 3.0, 1.0 to 2.5, 1.1 to 2.0, 1.3 to 1.8, or 1.5 to 1.7 equivalents of 1,4-cyclohexadiene is used for every 1 equivalent of the compound of formula (I) or (IA). In another embodiment, 1,4-cyclohexadiene was added portionwise. In another embodiment, 1,4-cyclohexadiene was added portionwise in 2 portions, in 3 portions, in 4 portions, or in 5 portions. In another embodiment, 1,4-cyclohexadiene was added portionwise in 2 portions, in 3 portions, in 4 portions. In another embodiment, 1,4-cyclohexadiene was added portionwise in 2 portions of 1.0 to 4.5, 1.0 to 4.0, 1.0 to 3.5, 1.0 to 3.0, 1.0 to 2.5, 1.1 to 2.0, 1.3 to 1.8, or 1.5 to 1.7 equivalents. In another embodiment, 1,4-cyclohexadiene was added portionwise in 2 portions of 1.0 to 2.0 equivalents. In another embodiment, 1,4-cyclohexadiene was added portionwise in 2 portions of 1.5 equivalents. In another embodiment, 1,4-cyclohexadiene was added portionwise in 3 portions of 1.0 to 4.5, 1.0 to 4.0, 1.0 to 3.5, 1.0 to 3.0, 1.0 to 2.5, 1.1 to 2.0, 1.3 to 1.8, or 1.5 to 1.7 equivalents. In another embodiment, 1,4-cyclohexadiene was added portionwise in 3 portions of 1.0 to 2.0 equivalents. In another embodiment, 1,4-cyclohexadiene was added portionwise in 3 portions of 1.5 equivalents.

In a 9$^{th}$ specific embodiment, for the method of the third, fourth, fifth or sixth embodiment or the 1st, 2$^{nd}$, 3$^{rd}$, 4$^{th}$, 5$^{th}$, or 6$^{th}$ specific embodiment, the de-benzylation reaction comprises reacting the compound of formula (I) or (IA) with 1,4-cyclohexadiene in the presence of a Pd/Alox catalyst (e.g., 5% Pd/Alox), and wherein 1.1 to 2.0 equivalent of 1,4-cyclohexadiene and 0.05 to 0.25 equivalent of Pd are used for every 1 equivalent of the compound of formula (I) or (IA). In a more specific embodiment, 1.3 to 1.8 equivalent of 1,4-cyclohexadiene and 0.05 to 0.2 equivalent of a Pd/Alox catalyst (e.g., 5% Pd/Alox) are used for every 1 equivalent of the compound of formula (I) or (IA). In another more specific embodiment, 1.5 to 1.7 equivalent of 1,4-cyclohexadiene and 0.075 to 0.15 equivalent of a Pd/Alox catalyst (e.g., 5% Pd/Alox) are used for every 1 equivalent of the compound of formula (I) or (IA). In a 10$^{th}$ specific embodiment, for the method of the third, fourth, fifth or sixth embodiment or the 1$^{st}$, 2$^{nd}$, 3$^{rd}$, 4$^{th}$, 5$^{th}$, 6$^{th}$, 7$^{th}$, 8$^{th}$ or 9$^{th}$ specific embodiment, the de-benzylation reaction is carried out in a solvent or a mixture of solvents. Any suitable solvents described herein can be used. Exemplary solvents include, but are not limited to, tetrahydrofuran (THF), 2-methyltetrahydrofuran (MeTHF), N-methyl-2-pyrrolidone (NMP), methanol, ethanol, isopropanol, dichloromethane, dichloroethane, acetonitrile, dimethylformamide (DMF), dimethylacetamide, cyclopentyl methyl ether (CPME), ethyl acetate, water, and a combination thereof. In a more specific embodiment, the de-benzylation reaction is carried out in a solvent mixture comprising a Pd-catalyst poison such as lead, copper, sulfur, sulfur-containing compounds, nitrogen-containing heterocycles or amines. In some embodiments, the Pd-catalyst poison is a thiol, thophene, pyridine, quinoline, 3,6-dithia-1,8-octanediol or DMSO. In an even more specific embodiment, the de-benzylation reaction is carried out in a mixture of DMSO and ethanol. DMSO can be present in a very small amount. For example, the solvent mixture (e.g., DMSO and ethanol) can have 0.01-1%, 0.05-0.75%, 0.1-0.5%, 0.1-0.3% or 0.1-0.2% by volume of DMSO.

In a 11$^{th}$ specific embodiment, for the method of the third, fourth, fifth or sixth embodiment or the 1$^{st}$, 2$^{nd}$, 3$^{rd}$, 4$^{th}$, 5$^{th}$, 6$^{th}$, 7$^{th}$, 8$^{th}$, 9$^{th}$ or 10$^{th}$ specific embodiment, the de-benzylation reaction is carried out at a temperature between 30° C. and 90° C., between 40° C. and 70° C., between 40° C. and 60° C., or between 45° C. and 55° C. In a more specific embodiment, the reaction is carried out at 50° C.

In a 12$^{th}$ specific embodiment, for the method of the third, fourth, fifth or sixth embodiment or the 1$^{st}$, 2$^{nd}$, 3$^{rd}$, 4$^{th}$, 5$^{th}$, 6$^{th}$ or 7$^{th}$ specific embodiment, the de-benzylation reaction of the compound of formula (I) or (IA) is carried out in the presence of 1,4-cyclohexadiene and a palladium catalyst (e.g., those described in the 5$^{th}$ or 6$^{th}$ specific embodiment, such as a Pd/Alox catalyst (e.g., 5% Pd/Alox)) and 1,4-cyclohexadiene is added portionwise. In a more specific embodiment, 1.1 to 2.0 equivalents (e.g., between 1.4 to 1.6 equivalents, or 1.1, 1.2, 1.3, 1.4, 1.5, 1.6, 1.7, 1.8, 1.9 or 2.0 equivalents) of 1,4-cyclohexadiene is first added to the compound of formula (I) or (IA) in the presence of a palladium catalyst (e.g., 5% Pd/Alox) and the reaction mixture is heated to an elevated temperature (e.g., between 40 and 60° C.) for 1 hour to 24 hours (e.g., 1 hour, 2 hours, 3 hours, 4 hours, 5 hours, 10 hours, 15 hours, 20 hours or 24 hours). After cooling (e.g., to room temperature), an additional 1.1 to 2.0 equivalents (e.g., between 1.4 to 1.6 equivalents, or 1.1, 1.2, 1.3, 1.4, 1.5, 1.6, 1.7, 1.8, 1.9 or 2.0 equivalents) 1,4-cyclohexadiene is then added and the reaction mixture is heated to an elevated temperature (e.g., between 40 and 60° C.) for 1 hour to 24 hours (e.g., 1 hour, 2 hours, 3 hours, 4 hours, 5 hours, 10 hours, 15 hours, 20 hours or 24 hours). Optionally, a further 1.1 to 2.0 equivalents (e.g., between 1.4 to 1.6 equivalents, or 1.1, 1.2, 1.3, 1.4, 1.5, 1.6, 1.7, 1.8, 1.9 or 2.0 equivalents) 1,4-cyclohexadiene can be added and the reaction mixture is heated to an elevated temperature (e.g., between 40 and 60° C.) for 1 hour to 24 hours (e.g., 1 hour, 2 hours, 3 hours, 4 hours, 5 hours, 10 hours, 15 hours, 20 hours or 24 hours). In an even more specific embodiment, the de-benzylation reaction is carried out in a mixture of DMSO and ethanol. DMSO can be present in a very small amount. For example, the solvent mixture (e.g., DMSO and ethanol) can have 0.01-1%, 0.05-0.75%, 0.1-0.5%, 0.1-0.3% or 0.1-0.2% by volume of DMSO.

In a 13$^{th}$ specific embodiment, for the method of the third, fourth, fifth or sixth embodiment, or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ or 12$^{th}$ specific embodiment, the compound of formula (III) or (IIIA) can be purified by precipitation. In a more specific embodiment, the compound is purified by precipitating the compound from an ethylacetate (EtOAc) solution containing the compound using water. In a even more specific embodiment, the volume of water used for precipitation is 1-10% (1-5%, 2-5%, 1%, 2%, 3%, or 4%) by volume of EtOAc.

In a 14$^{th}$ specific embodiment, for the method of the third, fourth, fifth or sixth embodiment, or the 1$^{st}$, 2$^{nd}$, 3$^{rd}$, 4$^{th}$, 5$^{th}$, 6$^{th}$, 7$^{th}$, 8$^{th}$, 9$^{th}$, 9$^{th}$, 10$^{th}$, 11$^{th}$, 12$^{th}$ or 13$^{th}$ specific embodiment, the method further comprising reducing the compound of formula (III) to form a compound of formula (VI):

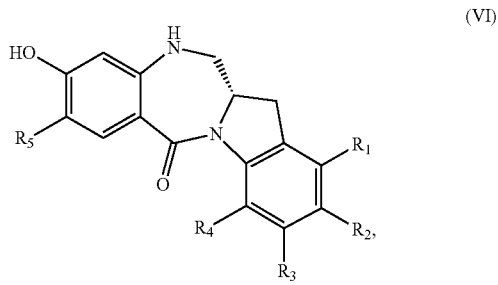

(VI)

or a salt thereof. In some embodiment, the compound of formula (III) is reduced using a suitable reducing agent. Exemplary reducing agents include, but are not limited to sodium borohydride, sodium triacetoxy borohydride, sodium cyanoborohydride, lithium aluminum hydride (LiAlH$_4$), hydrogen gas, ammonium formate, borane (BH$_3$), diborane (B$_2$H$_6$), borane-dimethylsulfide (DMS) complex, borane-amine complexes (e.g., ammonia borane (or borazane), borane trimethylamine complex, borane N,N-diisopropylethylamine complex, or borane tert-butylamine complex), 9-borabicyclo[3.3.1]nonane (9-BBN), diisobutylaluminium hydride (DIBAL), lithium borohydride (LiBH$_4$), potassium borohydride (KBH$_4$), sodium bis(2-methoxyethoxy)aluminumhydride (Red-Al), silicon-based reducing agent (e.g., PhSiH$_3$, Ph$_2$SiH$_2$ or Et$_3$SiH). In some embodiments, the reduction is carried out in a presence of a catalyst, such as a ruthenium catalyst, a rhodium catalyst or an iridium catalyst, etc. In a more specific embodiment, the compound of formula (III) is reacted with BH$_3$ (e.g., BH$_3$•THF solution) to form the compound of formula (VI) or a salt thereof. In an even more specific embodiment, excess amount of BH$_3$ relative to the compound of formula (III) is used. For example, 1.0 to 2.0 equivalents, 1.0 to 1.5 equivalents, or 1.1 to 1.3 equivalents of BH$_3$ can be used. In one embodiment, 1.2 equivalents of BH$_3$ is used. The reduction reaction can be carried out in any suitable organic solvent. In one embodiment, the reduction reaction is carried out in THF. The reaction can be carried out at a suitable temperature, for example, between 10° C. to 30° C., or between 15° C. to 25° C. In one embodiment, the reaction is carried out at 20° C. The reduction reaction can be carried out for 10 minutes to 10 hours, for example, for 30 minutes to 5 hours, for 30 minutes to 3 hours, or for 30 minutes to 2 hours. In another embodiment, the reaction is carried out for 1 hour or 2 hours. In another embodiment, upon completion, the reaction is quenched with saturatured NH$_4$Cl solution. In yet another embodiment, the compound of formula (VI) or a salt thereof can be purified by precipitation of the compound from a 2-methyltetrahydrofuran (MeTHF) solution containing the compound using heptane. In some embodiment, the compound of formula (VI) can be purified by azeotropic distillation with MeTHF to remove water.

In one embodiment, for the method described in the 14$^{th}$ specific embodiment above, the compound of formula (III) is represented by formula (IIIA):

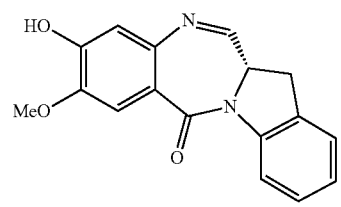 [SMILES: COc1cc2c(cc1O)N=C[C@@H]1Cc3ccccc3N1C2=O]

and the method comprising reducing the compound of formula (IIIA) to form the compound of formula (VIA):

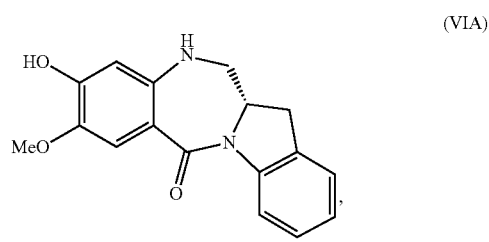 [SMILES: COc1cc2c(cc1O)NC[C@@H]1Cc3ccccc3N1C2=O]

(VIA)

or a salt thereof.

In a 15$^{th}$ specific embodiment, for the method of the first or fifth embodiment, or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$ or 14$^{th}$ specific embodiment, the compound of formula (II) is prepared by a method comprising the following steps:

a) reducing the compound of formula (IV):

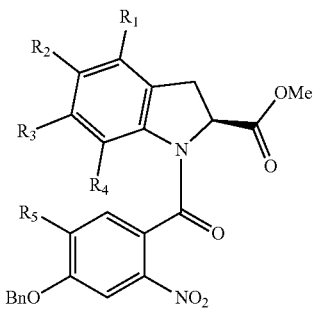
(IV)

with a reducing agent to form the compound of formula (V):

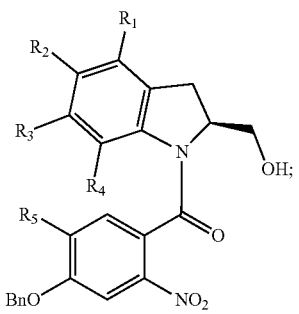
(V)

and b) oxidizing the compound of formula (V) with an oxidizing agent to form the compound of formula (II).

Also in the 15th specific embodiment, for the method of the second or sixth embodiment, 1st, 2nd, 3rd, 4th, 5th, 6th, 7th, 8th, 9th, 10th, 11th, 12th, 13th or 14th specific embodiment, the compound of formula (IIA) is prepared by a method comprising the following steps:

a) reducing the compound of formula (IVA):

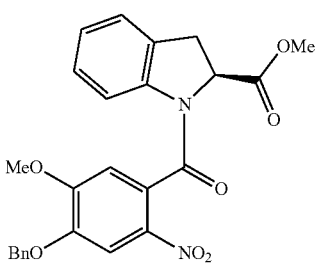
(IVA)

with a reducing agent to form the compound of formula (VA):

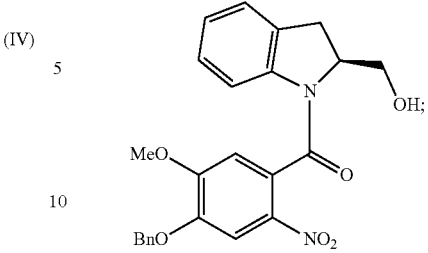
(VA)

and b) oxidizing the compound of formula (VA) with an oxidizing agent to form the compound of formula (IIA).

In a 16th specific embodiment, for the method described in the 15th specific embodiment, the reducing agent in the reaction of step a) is a hydride reducing agent. In another embodiment, the reducing agent is sodium borohydride, sodium triacetoxy borohydride, sodium cyanoborohydride, lithium aluminum hydride, hydrogen gas, ammonium formate, borane, 9-borabicyclo[3.3.1]nonane (9-BBN), diisobutylaluminium hydride (DIBAL), lithium borohydride (LiBH$_4$), potassium borohydride (KBH$_4$), or sodium bis(2-methoxyethoxy)aluminumhydride (Red-Al). In a more specific embodiment, the reducing agent is sodium borohydride.

In one embodiment, excess amount of the reducing agent relative to the compound of formula (IV) or (IVA) can be used. For example, 1.1 to 10 equivalents, 1.5 to 5 equivalents, 2.0 to 4.0 equivalents, or 2.5 to 3.5 equivalents of the reducing agent can be used for every 1 equivalent of the compound of formula (IV) or (IVA).

The reduction reaction of step a) can be carried out in a suitable solvent or solvent mixtures described herein. In one embodiment, the reaction is carried out in the mixture of THF and ethanol.

The reduction reaction can be carried out at a suitable temperature, for example, at a temperature between 0° C. to 50° C., between 0° C. to 30° C., or between 10° C. to 25° C. In one embodiment, the reduction reaction is carried out at room temperature or 20° C.

In a 14th specific embodiment, for the method described in the 12th or 13th specific embodiment, the oxidizing agent in the reaction of step b) is Dess-Martin periodinane (DMP), 2-iodoxybenzoic acid, Collins reagent (CrO$_3$•Py$_2$), pyridinium dichromate (PDC), pyridinium chlorochromate (PCC), tetrapropylammonium perruthenate (TPAP)/N-methylmorpholine N-oxide (NMO), (2,2,6,6-tetramethylpiperidin-1-yl)oxyl (TEMPO)/NaClO, DMSO/oxalyl chloride, DMSO/carbodiimide or DMSO/SO$_3$•Py. In a more specific embodiment, the oxidizing agent is DMP.

In one embodiment, excess amount of the oxidizing agent relative to the compound of formula (V) can be used. For example, 1.01 to 10 equivalent, 1.01 to 5 equivalent, 1.05 to 2.0 equivalent, or 1.1 to 1.5 equivalent of the oxidizing agent can be used for every 1 equivalent of the compound of formula (V).

The oxidation reaction of step b) can be carried out in a suitable solvent or solvent mixtures described herein. In one embodiment, the reaction is carried out in dichloromethane.

The oxidation reaction can be carried out at a suitable temperature, for example, at a temperature between 0° C. to 50° C., between 0° C. to 30° C., or between 10° C. to 25° C. In one embodiment, the oxidation reaction is carried out at room temperature or 20° C.

3. Compounds of the Invention

The present invention also provides compounds described herein. In one embodiment, the present invention is directed to compounds of formula (IV), (IVA), (V) or (VA) or a salt thereof.

All references cited herein and in the examples that follow are expressly incorporated by reference in their entireties.

4. Examples

The invention will now be illustrated by reference to non-limiting examples. Unless otherwise stated, all percentages, ratios, parts, etc. are by weight.

The following solvents, reagents, protecting groups, moieties and other designations may be referred to by their abbreviations in parenthesis:

aq=aqueous
Bn=benzyl
BnBr=benzyl bromide
$CH_3CN$=acetonitrile
DCM or $CH_2Cl_2$=dichloromethane
DMF=dimethylformamide
DMP=Dess-Martin periodinane
EtOAc=ethylacetate
$Et_3N$=triethylamine
g=grams
h=hour
HPLC=high-performance liquid chromatography
LC=liquid chromatography
LCMS=liquid chromatography mass spectrometry
min=minutes
mg=miligrams
mL=mililiters
mmol=milimoles
mol=moles
Me=methyl
MePH=methanol
MS=mass spectrometry
NMR=nuclear magnetic resonance spectroscopy
RT or rt=room temperature (ambient, about 25° C.)
sat or sat'd=saturated
SFC=supercritical fluid chromatography
THF=tetrahydrofuran
TLC=thin layer chromatography Example 1. Synthesis of Compound IIIA Step 1:

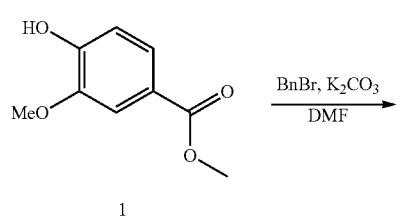

To a solution of compound 1 (500 g, 2.74 mol) in DMF (2.50 L) was added $K_2CO_3$ (757.39 g, 5.48 mol) in one portion, following BnBr (702.93 g, 4.11 mol, 488.15 mL) was added to the mixture in portions, the mixture was stirred at 20° C. for 72 h. TLC (petroleum ether: ethyl acetate=5:1) showed that the reaction was completed. The mixture was quenched by pouring into ice-water (3 L) and the precipitated solid was collected by filtration, the filter cake was triturated with petroleum (500 mL×2). Filtered and dried under vacuum to give compound 2 (1.00 kg, crude) as a white solid which was used in the next step without any further purification. $^1$H NMR: ($CDCl_3$ 400 MHz): δ 7.62-7.59 (dd, $J_1$=2.0 Hz, $J_2$=8.4 Hz, 1 H), 7.57-7.56 (d, J=2.0 Hz, 1 H), 7.44-7.26 (m, 5 H), 6.91-6.89 (d, J=8.4 Hz, 1 H), 5.21 (s, 2 H), 3.94 (s, 3 H), 3.88 (s, 3 H).

Step 2:

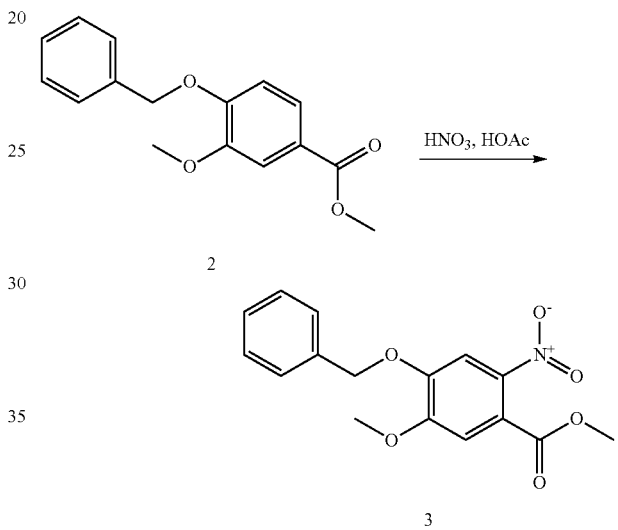

To a solution of compound 2 (200 g, 734.48 mmol) in $CH_3COOH$ (1.0 L) was slowly added $HNO_3$ (92.56 g, 1.47 mol, 66.11 mL) at 0-10° C. cooling with an ice bath. After the addition, concentrated $H_2SO_4$ (108.06 g, 1.10 mol, 58.73 mL) was drop wise added to the mixture at 0-10° C. until yellow solid precipitated. The mixture was then allowed to be warmed to 20° C. and stirred for 3 h. TLC (petroleum ether: ethyl acetate=5:1) showed that the reaction was completed. The mixture was slowly poured into a stirred ice-water (3 L) to give a slurry. The solid was collected by filtration. Dried under vacuum to give compound 3 (250 g, crude) as a yellow solid.

Step 3:

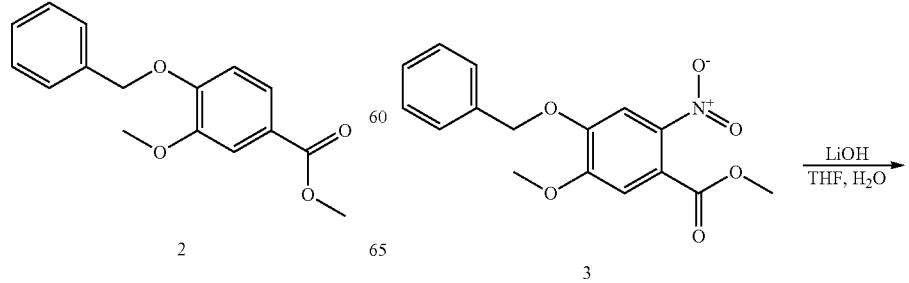

-continued

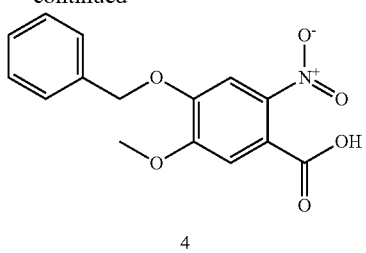

4

To a solution of compound 3 (2.50 kg, 7.93 mol) in THF (20 L) and H₂O (20 L) was added LiOH•H₂O (332.68 g, 7.93 mol) in one portion at 20° C. to give a suspension, the reaction was stirred at this temperature for 16 h. TLC (petroleum ether: ethyl acetate=2:1) showed that the reaction was completed. The solvent was evaporated under vacuum to remove THF. The residue was acidified with 2N HCl until pH=2 to give a yellow precipitated. The solid was collected by filtration, washed with H₂O (10 L), the filtrate cake was dissolved in CH₂Cl₂ (15 L) and THF (3 L), separated to removed H₂O, dried over Na₂SO₄, concentrated under high vacuum to give compound 4 (1.5 kg, 62.39% yield) as a yellow solid. ¹H NMR: (DMSO-d₆ 400MHz): δ 7.69 (s, 1 H), 7.47-7.36 (m, 5 H), 7.30 (s, 1 H), 5.23 (s, 2 H), 3.91 (s, 3 H).

Step 4:

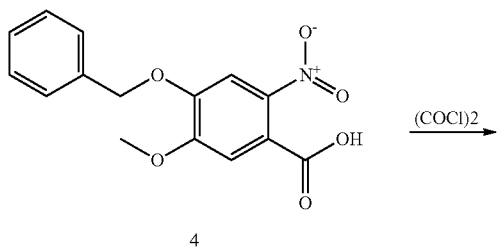

4

(COCl)2 →

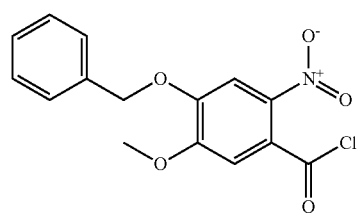

5

To a solution of compound 4 (500 g, 1.65 mol) in CH₂Cl₂ (2.0 L) and THF (500 mL) was added DMF (6.03 g, 82.50 mmol), cooled with ice-water bath to 0-10° C. (COCl)₂ (418.54 g, 3.30 mol, 288.65 mL) was drop wise added to the mixture maintaining the temperature between 0-10° C. The mixture was then warmed to 20° C. and stirred at this temperature for 16 h. TLC (petroleum ether: ethyl acetate=2:1) showed that the reaction was completed. The solvent was removed under vacuum to give compound 5 (550 g, crude) as a yellow solid.

Step 5:

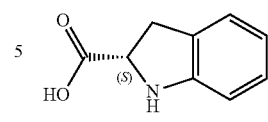

6

SOCl₂, MeOH →

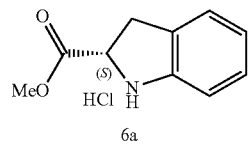

6a

To a mixture of compound 6 (1.00 kg, 6.13 mol) in MeOH (10 L) was added SOCl₂ (1.46 kg, 12.26 mol, 889.37 mL) drop wise at 0° C. After the addition, the result mixture was stirred at 25° C. for 16 h. TLC (petroleum ether: ethyl acetate=1:1, Rf=0.47) showed the reaction was completed. 5 batches of such reaction mixture were combined and concentrated under reduced pressure to dryness. Compound 6a (5.21 kg, 89.50% yield, HCl) was obtained as grey solid.

Step 6:

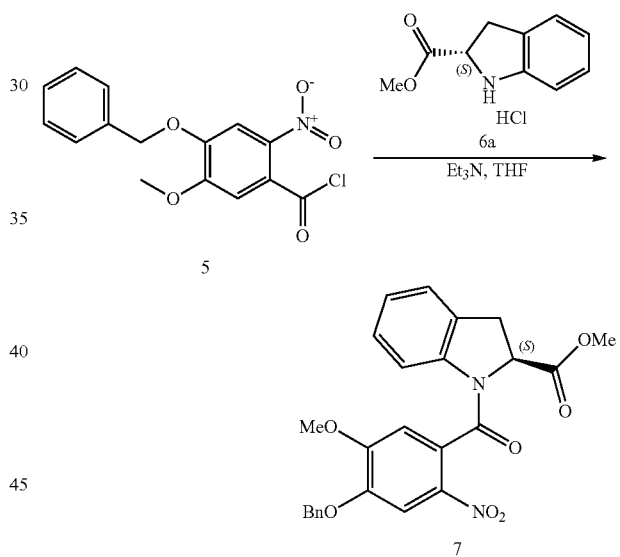

A solution of compound 6a (2.71 kg, 12.68 mol) in THF (8.0 L) was cooled to 0-10° C., added Et₃N (4.01 kg, 39.63 mol, 5.49 L) in portions maintaining the temperature below 10° C. The mixture was stirred at this temperature for 30 min, a solution of compound 5 (4.40 kg, 13.21 mol) in THF (16.0 L) was added dropwise at 0-10° C. After the addition, the result reaction mixture was allowed to be warmed to 20° C. and stirred for 16 h. TLC (petroleum ether: ethyl acetate=2:1) showed that the reaction was completed. The mixture was quenched with H₂O (10 L), THF was removed under vacuum, the aqueous layer was extracted with EtOAc (10 L×3), the combined organic layers were and washed with brine (10 L), dried over Na₂SO₄, concentrated to give a black brown oil. The oil was recrystallized with MeOH (15 L), filtered and dried under vacuum to give compound 7 (3.38 kg, 55.34% yield) as a yellow solid. ¹H NMR: (DMSO-d₆, 400 MHz): δ 8.12-7.91 (m, 1 H), 7.52-6.89 (m, 8 H), 5.33-5.29 (m, 2 H), 5.1-4.7 (m, 1 H), 3.94-3.91 (m, 2

H), 3.76-3.64 (m, 2 H), 3.61 (s, 3 H), 3.19-3.13 (m, 1 H). HPLC: 99.16%. LC-MS: MS (ESI, m/z): 485.1 (M+23)+. SFC: 100% ee

Step 7:

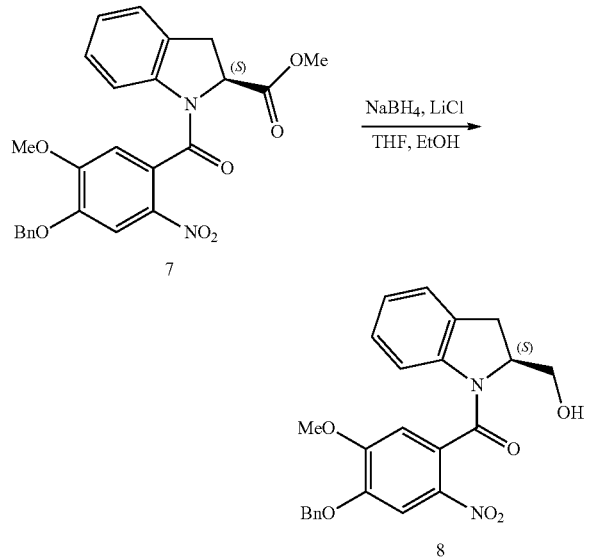

To a mixture of THF (17 L) and EtOH (17 L) was added compound 7 (1.69 kg, 3.65 mol), cooled to 0-10° C. LiCl (309.45 g, 7.30 mol) was added to the mixture in one portion. NaBH$_4$ (345.20 g, 9.13 mol) was added portionwise to the mixture maintaining the temperature at 0-10° C. After the addition, the mixture was warmed to 20° C. and stirred for 16 h. TLC (petroleum ether: ethyl acetate=1:1) showed that the reaction was completed. The mixture was poured into H$_2$O (10 L), the solvent was evaporated under vacuum to remove most of THF and EtOH. The residue was extracted with CH$_2$Cl$_2$ (10 L×3), the organic layers were combined and dried over Na$_2$SO$_4$, concentrated to give a yellow solid. The crude product was purified on silica gel by column chromatography (eluted from petroleum ether/ethyl acetate/dichloromethane =50/12/1 to dichloromethane/methanol=10/1) to give a yellow solid. The solid was triturated with EtOAc (5 L) for 16 h. Filtrated and dried under vacuum to give compound 8 (2.11 kg, 66.21% yield) as a yellow solid. $^1$H NMR: (DMSO-d$_6$, 400 MHz): δ 8.04-7.85 (m, 2 H), 7.51-7.36 (m, 7 H), 7.32-7.22 (m, 2 H), 7.12-7.09 (m, 1 H), 6.96-6.80 (m, 1 H), 5.31-5.25 (m, 2 H), 5.03-4.79 (m, 2 H), 3.98-3.95 (m, 3 H), 3.32-2.95 (m, 4 H). HPLC: 98.51%. LCMS: (ESI, m/z): 457 (M+H)+. SFC: 100% ee.

Step 8:

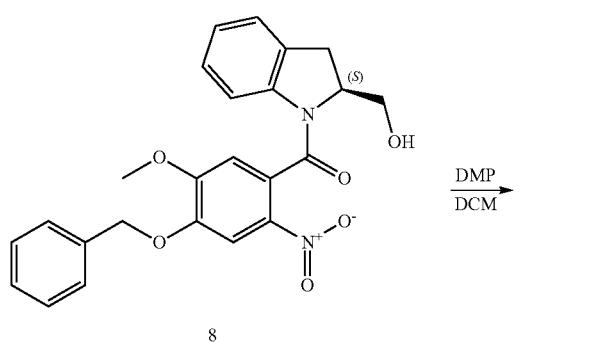

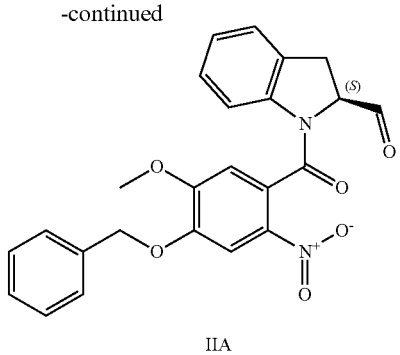

To a solution of compound 8 (4.30 kg, 9.90 mol) in DCM (25 L) was added NaHCO$_3$ (557.11 g, 6.63 mol) in one portion. DMP (5.04 kg, 11.88 mol) was added in portions and the result mixture was stirred at 20° C. for 16 h. TLC (petroleum ether: ethyl acetate=1:1) showed that the reaction was completed. The mixture was poured into sat. Na$_2$S$_2$O$_3$ (7.5 kg in 25 L) to consume the excess DMP. The solvent was separated and the aq. layer was extracted with DCM (5 L×3), the combined organic layers were washed with brine (10 L×3), separated and dried over Na$_2$SO$_4$, concentrated to give black brown oil. The crude oil was triturated with EtOAc (5 L). Filtrated and dried under vacuum to give compound IIA (3.50 kg, 81.76% yield) as a yellow solid. $^1$H NMR: (CDCl$_3$, 400 MHz): δ 10.00-9.44 (m, 1 H), 7.92-7.77 (m, 2 H), 7.49-6.82 (m, 9 H), 5.77-5.22 (m, 3 H), 4.12-3.93 (m, 3 H), 3.50-3.25 (m, 2 H). HPLC: 92.15%. SFC: 100% ee.

Step 9:

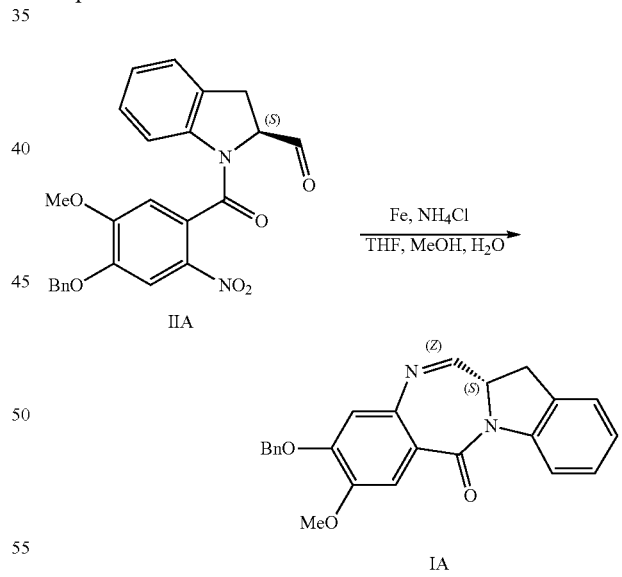

To a solution of compound IIA (1.10 kg, 2.54 mol) in THF (3.30 L), MeOH (16.50 L) and H$_2$O (3.30 L) was added NH$_4$Cl (1.36 kg, 25.40 mol) in one portion at 20° C. Fe (425.58 g, 7.62 mol) was added portion wise to the mixture at 20° C. After the addition, the mixture was heated to 65° C. and stirred under N$_2$ atmosphere for 48 h. HPLC showed that the reaction was completed. The mixture was cooled to 20° C. and poured into DCM (10 L) to give a black suspension, filtrated on celite; the filtrate was evaporated under high vacuum to remove THF and MeOH. The filter cake was dispersed in DCM (15 L×2) and stirred at 45° C. for 1 h. Filtrated and the filtrate was combined with the a.q. layer. The combined layers were washed with H₂O (10 L), brine (10 L), separated and dried over Na₂SO₄, concentrated to give a brown solid. The solid was recrystallized in DCM/EtOH (1/1, 5 L) overnight, filtrated and dried under vacuum to give compound IA (720 g, 71.63% yield, 97.15% purity) as a brown solid. The crude was re-crystallized following below procedure. 300 g crude was dissolved in toluene (1.20 L) and heated to 80° C. rapidly, the mixture was stirred at 80° C. for 10 min and filtrated when hot, CH₃CN (1.80 L) was slowly added to the mixture within 10 min and large amount solid precipitated, the temperature was cooled to 60° C. after the addition. The mixture was cooled to 20° C., stirred at this temperature for 16 h. Two batches of such solid was filtrated and washed with CH₃CN (200 mL×3), dried under high vacuum to give compound IA (465.85 g, 1.21 mol, 77.64% yield) as an off white solid.

¹H NMR: (CDCl₃, 400 MHz): δ 8.28-8.26 (d, J=8.0 Hz, 1 H), 7.86-7.85 (d, J=4.0 Hz, 1 H), 7.58 (s, 1 H), 7.47-7.25 (m, 7 H), 7.13-7.09 (m, 1 H), 6.87 (s, 1 H), 5.27-5.19 (m, 2 H), 4.49-4.44 (m, 1 H), 3.98 (s, 3 H), 3.74-3.67 (m, 1 H), 3.51-3.46 (m, 1 H). HPLC purity: 96.38%.

Step 10:

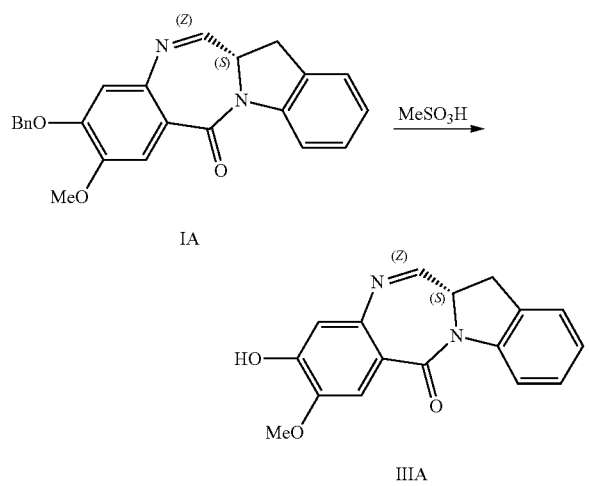

To a 100 mL round-bottom flask charged with methane-sulfonic acid (67.50 g, 702.32 mmol, 50.0 mL) was added compound IA (5.0 g, 13.01 mmol, 18 batches) in one portion, the mixture was stirred at 20° C. for 1 h. TLC (petroleum ether: ethyl acetate=1:1) showed that the reaction was completed. The mixture was poured into sat. CH₃COONa (8 kg in 40 L water) to adjust pH=6-7 with yellow solid precipitated. The solid was collected by filtration to give compound IIIA (60.00 g, crude) as a yellow solid. The crude was re-crystallized following below procedure. (55 g, 374.76 mmol, 2 batches) was dissolved into 5 L DCE (heated to 100° C.), filtrated while hot, the filtrate was concentrated under vacuum to give a yellow solid. The solid was re-dissolved into DCM (500 mL), H₂O (500 mL) was added to the solution and large amount of yellow solid was precipitated out, filtrated and the filter cake was triturated with CH₃CN (500 mL) for 1 h. Filtrated and dried under high vacuum to give compound IIIA (90.0 g, 81.82% yield) as an off white solid. ¹H NMR: (CDCl3 400 MHz): δ 8.30-8.28 (d, J=8.0 Hz, 1 H), 7.91-7.90 (d, J=4.0 Hz, 1 H), 7.58 (s, 1 H), 7.32-7.28 (m, 2 H), 7.15-7.11 (m, 1 H), 6.94 (s, 1 H), 6.16 (s, 1 H), 4.52-4.47 (m, 1 H), 4.00 (s, 3 H), 3.76-3.69 (m, 1 H), 3.55-3.50 (m, 1 H). HPLC: 96.79%. SFC: 100% ee.

Example 2. Debenzylation of Compound IA

To a suspension of (12aS)-9-benzyloxy-8-methoxy-12a,13-dihydroindolo[2,1-c][1,4]benzodiazepin-6-one (compound IA, 80 g, 188.02 mmol) and DMSO (1.32 g, 16.92 mmol, 1.32 mL, 0.09 eq) in EtOH (200 mL) were added Pd/Alox (40.02 g, 18.80 mmol, 5% purity, 0.10 eq) and cyclohexa-1,4-diene (25 g, 312.12 mmol, 29.42 mL, 1.66 eq) at 25° C. under N₂ atmosphere. After the addition, the reaction was heated to 50° C. and stirred at 50° C. for 2 h under N₂ atmosphere. HPLC analysis showed the starting material was consumed completely.

After cooling, the reaction mixture was filtered and the filter cake was washed with EtOH (100 mL×4).The combined 2 batches of filtrate was concentrated under reduced pressure to give a residue.

The residue was dissolved in EtOAc (160 mL) and stirred at 25° C. for 15 min. Then, H₂O (5 mL) was slowly added to the mixture within 5 min and a large amount of solid precipitated. After addition, the reaction mixture was stirred at 25° C. for 120 hr. The solid was filtered and washed with EtOAc (50 mL×2) dried under high vacuum to give compound IIIA as a white solid (105 g, 337.87 mmol, 89.85% yield, 94.7% purity).

A suspension of compound IIIA (5.0 g, 17.0 mmol, 1.0 eq) in dichloroethane (75 mL) was heated to 100° C. and stirred at 100° C. for 1 h under N₂ atmosphere. After cooling to 25° C., the suspension was filtered and washed with dichloroethane (20 mL×2) dried under high vacuum to give compound IIIA (3.5 g, 75.0% yield) as a white solid.

In another experiment, compound IA (5.09 g, 1.0 eq) was suspended in EtOH (50.9 mL, 10 V) and DMSO (87 μL, 0.017 V) was added. 5% Pd/Alox was charged followed by adding cyclohexa-1,4-diene (1.7 mL, 1.5 eq) dropwise at room temperature. The reaction mixture was heated at 50° C. for 1 hour. After cooling down the reaction mixture, another portion of cyclohexa-1,4-diene (1.7 mL, 1.5 eq) was added and the mixture was allowed to warm up to 50° C. for 1 hour. After cooling down the reaction mixture, another portion of cyclohexa-1,4-diene (1.7 mL, 1.5 eq) was added and the mixture was allowed to warm up to 50° C. for 1 hour. The reaction mixture was cooled to room temperature and filtered over 0.45 μm filter cartridge and rinsed with EtOH (3×10 V). The organic solution was concentrated to dryness to afford a yellow foam. The foam was dissolved in EtOAc (10 V) and stored below −15° C. To the EtOAc solution of crude compound IIIA (4.04 g) was added water (0.3 V) and the resulting mixture was stirred at 20° C. The product precipitated out of the solution rapidly and the resulting thin yellow suspension was stirred. Filtration, rinsing with EtOAc (2 V) and drying under vacuum at 30° C. to give the final product (2,7 g, 97% purity).

Example 3. Reduction of Compound IIIA

Compound IIIA (23.25 g, 1 eq) was suspended in THF (233 mL, 10 V). BH₃•THF (1.05 M, 90.3 mL, 1.2 eq) was slowly added at ~21° C. The reaction mixture was stirred at 20° C.±5° C. for 1 h. The reaction mixture was quenched by addition of saturated NH₄Cl (5 V) followed by water (5 V). The organic phases were washed with 15% NaCl (2×5 V). The organic layer was then diluted with Me-THF (40 V) and washed with water (5 V). The organic layer was isolated and concentrated under vacuum down to 10 V. Co-evaporation with MeTHF was carried out to remove water (3×10 V). The resulting suspension was concentrated down to 5 V, followed by addition of heptane (40 V). The resulting slurry was stirred at 20° C., then filtered, rinsed with heptand and dried under vacuum at 30° C. to yield pale yellow solid (19.5 g, 99.14% purity).

The invention claimed is:

1. A method for preparing a compound of formula (I):

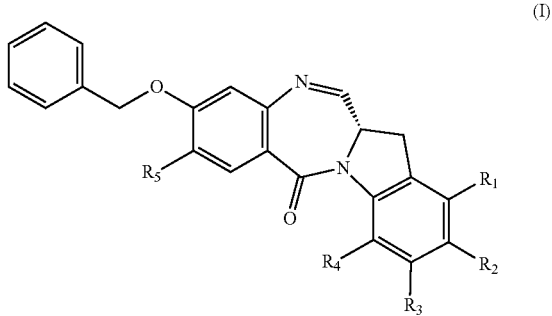

(I)

wherein:
R$_1$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_2$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_3$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_4$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_5$ is H, F, Cl, Br, I, NR'R'', OR, SR, or R;

R' is H, C$_{1-10}$ alkyl, (CH$_2$CH$_2$X)$_n$R$^c$, C$_{2-10}$ alkenyl, C$_{2-10}$ alkynyl, COR, NR$_2$, OR, C$_{3-10}$ cycloalkyl, C$_{4-10}$ cycloalkenyl, C$_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

R'' is H, C$_{1-10}$ alkyl, (CH$_2$CH$_2$X)$_n$R$^c$, C$_{2-10}$ alkenyl, C$_{2-10}$ alkynyl, COR, NR$_2$, OR, C$_{3-10}$ cycloalkyl, C$_{4-10}$ cycloalkenyl, C$_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

each R is independently H, C$_{1-10}$ alkyl, (CH$_2$CH$_2$X)$_n$R$^c$, C$_{2-10}$ alkenyl, C$_{2-10}$ alkynyl, C$_{3-10}$ cycloalkyl, C$_{4-10}$ cycloalkenyl, C$_{4-10}$ cycloalkynyl, C$_{6-18}$ aryl, 5- to 18-membered heteroaryl, or 3- to 18-membered heterocyclyl, wherein the 5- to 18-membered heteroaryl contains one or more heteroatoms independently selected from the group consisting of N, O, and S, and further wherein the 3- to 18-membered heterocyclyl contains 1, 2, 3, 4, 5, or 6 heteroatoms independently selected from the group consisting of N, O, S, and P;

each R$^c$ is independently H or C$_{1-4}$ alkyl;

each X is independently —NH—, —O—, or —S—; and each n is independently 1, 2, 3, 4, 5, 6, 7, 8, 9, 10, 11, 12, 13, 14, 15, 16, 17, 18, 19, 20, 21, 22, 23, or 24;

comprising the following step:

reacting a compound of formula (II):

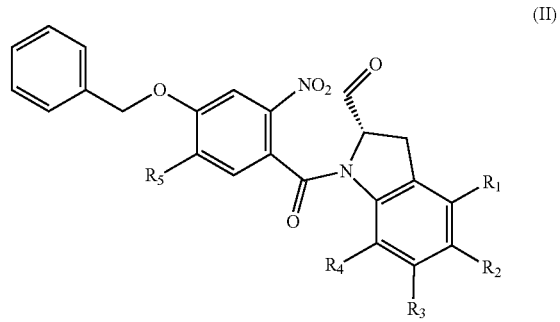

(II)

wherein:
R$_1$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_2$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_3$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_4$ is H, F, Cl, Br, I, CN, C$_{1-10}$ alkyl, C$_{2-10}$ alkenyl, C$_{2-10}$ alkynyl, COR', NR'R'', NR'COR'', NH(C=NH)NH$_2$, NCO, N$_3$, (XCH$_2$CH$_2$)$_n$R$^c$, OR, OCOR', OCONR'R'', OSO$_3$H, SR, SOR', SO$_2$R', SO$_2$NR'R'', SO$_3$H, C$_{3-10}$ cycloalkyl, C$_{4-10}$ cycloalkenyl, or C$_{4-10}$ cycloalkynyl;

R$_5$ is H, F, Cl, Br, I, NR'R'', OR, SR, or R;

R' is H, C$_{1-10}$ alkyl, (CH$_2$CH$_2$X)$_n$R$^c$, C$_{2-10}$ alkenyl, C$_{2-10}$ alkynyl, COR, NR$_2$, OR, C$_{3-10}$ cycloalkyl, C$_{4-10}$ cycloalkenyl, C$_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

R'' is H, C$_{1-10}$ alkyl, (CH$_2$CH$_2$X)$_n$R$^c$, C$_{2-10}$ alkenyl, C$_{2-10}$ alkynyl, COR, NR$_2$, OR, C$_{3-10}$ cycloalkyl, $C_{4-10}$ cycloalkenyl, $C_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

each R is independently H, $C_{1-10}$ alkyl, $(CH_2CH_2X)_nR^c$, $C_{2-10}$ alkenyl, $C_{2-10}$ alkynyl, $C_{3-10}$ cycloalkyl, $C_{4-10}$ cycloalkenyl, $C_{4-10}$ cycloalkynyl, $C_{6-18}$ aryl, 5- to 18-membered heteroaryl, or 3- to 18-membered heterocyclyl, wherein the 5- to 18-membered heteroaryl contains one or more heteroatoms independently selected from the group consisting of N, O, and S, and further wherein the 3- to 18-membered heterocyclyl contains 1, 2, 3, 4, 5, or 6 heteroatoms independently selected from the group consisting of N, O, S, and P;

each $R^c$ is independently H or $C_{1-4}$ alkyl;

each X is independently —NH—, —O—, or —S—; and each n is independently 1, 2, 3, 4, 5, 6, 7, 8, 9, 10, 11, 12, 13, 14, 15, 16, 17, 18, 19, 20, 21, 22, 23, or 24;

with Fe in the presence of $NH_4Cl$, to form the compound of formula (I) above.

2. The method of claim 1, wherein:
$R_1$ is H;
$R_2$ is H;
$R_3$ is H;
$R_4$ is H; and
$R_5$ is $OCH_3$.

3. The method of claim 1, wherein the reaction is performed under an inert atmosphere.

4. The method of claim 1, wherein the reaction is performed in a solvent selected from the group consisting of tetrahydrofuran, 2-methyltetrahydrofuran, N-methyl-2-pyrrolidone, methanol, ethanol, isopropanol, dichloromethane, dichloroethane, acetonitrile, dimethylformamide, dimethylacetamide, cyclopentyl methyl ether, ethyl acetate, and water, or a combination thereof.

5. The method of claim 4, wherein the reaction is performed in a mixture of tetrahydrofuran, methanol, and water.

6. The method of claim 1, wherein the reaction is performed at a temperature in the range of 40° C.-90° C.

7. A method for preparing a compound of formula (I):

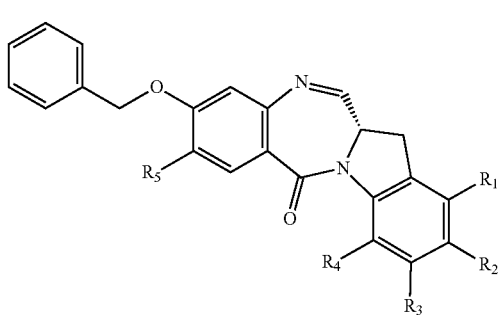

(I)

wherein:
$R_1$ is H, F, Cl, Br, I, CN, $C_{1-10}$ alkyl, $C_{2-10}$ alkenyl, $C_{2-10}$ alkynyl, COR', NR'R", NR'COR", $NH(C=NH)NH_2$, NCO, $N_3$, $(XCH_2CH_2)_nR^c$, OR, OCOR', OCONR'R", $OSO_3H$, SR, SOR', $SO_2R'$, $SO_2NR'R"$, $SO_3H$, $C_{3-10}$ cycloalkyl, $C_{4-10}$ cycloalkenyl, or $C_{4-10}$ cycloalkynyl;

$R_2$ is H, F, Cl, Br, I, CN, $C_{1-10}$ alkyl, $C_{2-10}$ alkenyl, $C_{2-10}$ alkynyl, COR', NR'R", NR'COR", $NH(C=NH)NH_2$, NCO, $N_3$, $(XCH_2CH_2)_nR^c$, OR, OCOR', OCONR'R", $OSO_3H$, SR, SOR', $SO_2R'$, $SO_2NR'R"$, $SO_3H$, $C_{3-10}$ cycloalkyl, $C_{4-10}$ cycloalkenyl, or $C_{4-10}$ cycloalkynyl;

$R_3$ is H, F, Cl, Br, I, CN, $C_{1-10}$ alkyl, $C_{2-10}$ alkenyl, $C_{2-10}$ alkynyl, COR', NR'R", NR'COR", $NH(C=NH)NH_2$, NCO, $N_3$, $(XCH_2CH_2)_nR^c$, OR, OCOR', OCONR'R", $OSO_3H$, SR, SOR', $SO_2R'$, $SO_2NR'R"$, $SO_3H$, $C_{3-10}$ cycloalkyl, $C_{4-10}$ cycloalkenyl, or $C_{4-10}$ cycloalkynyl;

$R_4$ is H, F, Cl, Br, I, CN, $C_{1-10}$ alkyl, $C_{2-10}$ alkenyl, $C_{2-10}$ alkynyl, COR', NR'R", NR'COR", $NH(C=NH)NH_2$, NCO, $N_3$, $(XCH_2CH_2)_nR^c$, OR, OCOR', OCONR'R", $OSO_3H$, SR, SOR', $SO_2R'$, $SO_2NR'R"$, $SO_3H$, $C_{3-10}$ cycloalkyl, $C_{4-10}$ cycloalkenyl, or $C_{4-10}$ cycloalkynyl;

$R_5$ is H, F, Cl, Br, I, NR'R", OR, SR, or R;

R' is H, $C_{1-10}$ alkyl, $(CH_2CH_2X)_nR^c$, $C_{2-10}$ alkenyl, $C_{2-10}$ alkynyl, COR, $NR_2$, OR, $C_{3-10}$ cycloalkyl, $C_{4-10}$ cycloalkenyl, $C_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

R" is H, $C_{1-10}$ alkyl, $(CH_2CH_2X)_nR^c$, $C_{2-10}$ alkenyl, $C_{2-10}$ alkynyl, COR, $NR_2$, OR, $C_{3-10}$ cycloalkyl, $C_{4-10}$ cycloalkenyl, $C_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

each R is independently H, $C_{1-10}$ alkyl, $(CH_2CH_2X)_nR^c$, $C_{2-10}$ alkenyl, $C_{2-10}$ alkynyl, $C_{3-10}$ cycloalkyl, $C_{4-10}$ cycloalkenyl, $C_{4-10}$ cycloalkynyl, $C_{6-18}$ aryl, 5- to 18-membered heteroaryl, or 3- to 18-membered heterocyclyl, wherein the 5- to 18-membered heteroaryl contains one or more heteroatoms independently selected from the group consisting of N, O, and S, and further wherein the 3- to 18-membered heterocyclyl contains 1, 2, 3, 4, 5, or 6 heteroatoms independently selected from the group consisting of N, O, S, and P;

each $R^c$ is independently H or $C_{1-4}$ alkyl;

each X is independently —NH—, —O—, or —S—; and each n is independently 1, 2, 3, 4, 5, 6, 7, 8, 9, 10, 11, 12, 13, 14, 15, 16, 17, 18, 19, 20, 21, 22, 23, or 24;

comprising the following steps:
(a) reacting a compound of formula (II):

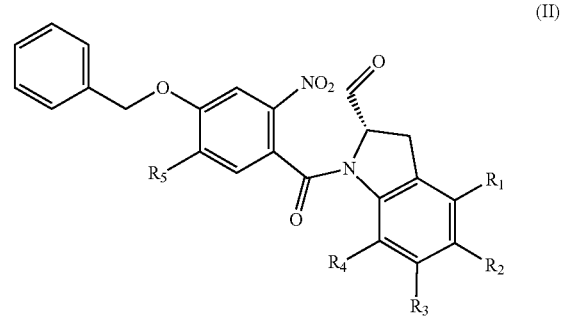

(II)

wherein:

$R_1$ is H, F, Cl, Br, I, CN, $C_{1-10}$ alkyl, $C_{2-10}$ alkenyl, $C_{2-10}$ alkynyl, COR', NR'R", NR'COR", NH(C=NH)NH$_2$, NCO, N$_3$, (XCH$_2$CH$_2$)$_n$R$^c$, OR, OCOR', OCONR'R", OSO$_3$H, SR, SOR', SO$_2$R', SO$_2$NR'R", SO$_3$H, $C_{3-10}$ cycloalkyl, $C_{4-10}$ cycloalkenyl, or $C_{4-10}$ cycloalkynyl;

$R_2$ is H, F, Cl, Br, I, CN, $C_{1-10}$ alkyl, $C_{2-10}$ alkenyl, $C_{2-10}$ alkynyl, COR', NR'R", NR'COR", NH(C=NH)NH$_2$, NCO, N$_3$, (XCH$_2$CH$_2$)$_n$R$^c$, OR, OCOR', OCONR'R", OSO$_3$H, SR, SOR', SO$_2$R', SO$_2$NR'R", SO$_3$H, $C_{3-10}$ cycloalkyl, $C_{4-10}$ cycloalkenyl, or $C_{4-10}$ cycloalkynyl;

$R_3$ is H, F, Cl, Br, I, CN, $C_{1-10}$ alkyl, $C_{2-10}$ alkenyl, $C_{2-10}$ alkynyl, COR', NR'R", NR'COR", NH(C=NH)NH$_2$, NCO, N$_3$, (XCH$_2$CH$_2$)$_n$R$^c$, OR, OCOR', OCONR'R", OSO$_3$H, SR, SOR', SO$_2$R', SO$_2$NR'R", SO$_3$H, $C_{3-10}$ cycloalkyl, $C_{4-10}$ cycloalkenyl, or $C_{4-10}$ cycloalkynyl;

$R_4$ is H, F, Cl, Br, I, CN, $C_{1-10}$ alkyl, $C_{2-10}$ alkenyl, $C_{2-10}$ alkynyl, COR', NR'R", NR'COR", NH(C=NH)NH$_2$, NCO, N$_3$, (XCH$_2$CH$_2$)$_n$R$^c$, OR, OCOR', OCONR'R", OSO$_3$H, SR, SOR', SO$_2$R', SO$_2$NR'R", SO$_3$H, $C_{3-10}$ cycloalkyl, $C_{4-10}$ cycloalkenyl, or $C_{4-10}$ cycloalkynyl;

$R_5$ is H, F, Cl, Br, I, NR'R", OR, SR, or R;

R' is H, $C_{1-10}$ alkyl, (CH$_2$CH$_2$X)$_n$R$^c$, $C_{2-10}$ alkenyl, $C_{2-10}$ alkynyl, COR, NR$_2$, OR, $C_{3-10}$ cycloalkyl, $C_{4-10}$ cycloalkenyl, $C_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

R" is H, $C_{1-10}$ alkyl, (CH$_2$CH$_2$X)$_n$R$^c$, $C_{2-10}$ alkenyl, $C_{2-10}$ alkynyl, COR, NR$_2$, OR, $C_{3-10}$ cycloalkyl, $C_{4-10}$ cycloalkenyl, $C_{4-10}$ cycloalkynyl, or 3- to 18-membered heterocyclyl, wherein the 3- to 18-membered heterocyclyl contains 1, 2, 3, 4, 5, or 6 heteroatoms independently selected from the group consisting of N, O, S, and P;

each R is independently H, $C_{1-10}$ alkyl, (CH$_2$CH$_2$X)$_n$R$^c$, $C_{2-10}$ alkenyl, $C_{2-10}$ alkynyl, $C_{3-10}$ cycloalkyl, $C_{4-10}$ cycloalkenyl, $C_{4-10}$ cycloalkynyl, $C_{6-18}$ aryl, 5- to 18-membered heteroaryl, or 3- to 18-membered heterocyclyl, wherein the 5- to 18-membered heteroaryl contains one or more heteroatoms independently selected from the group consisting of N, O, and S, and further wherein the 3- to 18-membered heterocyclyl contains 1, 2, 3, 4, 5, or 6 heteroatoms independently selected from the group consisting of N, O, S, and P;

each R$^c$ is independently H or $C_{1-4}$ alkyl;

each X is independently —NH—, —O—, or —S—; and each n is independently 1, 2, 3, 4, 5, 6, 7, 8, 9, 10, 11, 12, 13, 14, 15, 16, 17, 18, 19, 20, 21, 22, 23, or 24;

with Fe in the presence of NH$_4$Cl, to form the compound of formula (I) above; and (b) purifying the compound of formula (I) above by performing at least one recrystallization or at least one precipitation, or a combination thereof.

8. The method of claim 7, wherein:
$R_1$ is H;
$R_2$ is H;
$R_3$ is H;
$R_4$ is H; and
$R_5$ is OCH$_3$.

9. The method of claim 7, wherein the recrystallization or the precipitation in step (b) is performed in a mixture of acetonitrile and toluene.

10. The method of claim 7, wherein the recrystallization or the precipitation in step (b) is performed in a mixture of dichloromethane and ethanol.

11. The method of claim 10, wherein the ratio of the volume of dichloromethane to the volume of ethanol is 1:1.

12. The method of claim 7, wherein the recrystallization further comprises filtration.

13. A method for preparing a compound of formula (IA):

(IA)

comprising the following steps:
(a) reacting a compound of formula (IIA):

(IIA)

with Fe in the presence of NH$_4$Cl, to form the compound of formula (IA) above; and (b) purifying the compound of formula (IA) above by performing at least one recrystallization or at least one precipitation, or a combination thereof.

14. The method of claim 13, wherein the reaction in step (a) is performed in a mixture of tetrahydrofuran, methanol, and water.

15. The method of claim 14, wherein the reaction in step (a) is performed at a temperature in the range of 60° C.-70° C.

16. The method of claim 14, wherein the reaction in step (a) is performed at 65° C.

17. The method of claim 13, wherein the recrystallization or the precipitation in step (b) is performed in a mixture of acetonitrile and toluene.

18. The method of claim 17, wherein the recrystallization in step (b) comprises dissolving the compound of formula (IA) in toluene at a temperature in the range of 75° C.-85° C. and adding acetonitrile.

19. The method of claim 13, wherein the recrystallization or the precipitation in step (b) is performed in a mixture of dichloromethane and ethanol.

20. The method of claim 19, wherein the ratio of the volume of dichloromethane to the volume of ethanol is 1:1.

* * * * *